United States Patent
Jin et al.

(10) Patent No.: US 12,279,909 B2
(45) Date of Patent: Apr. 22, 2025

(54) METHODS AND SYSTEMS FOR ULTRASOUND PROBE POWER MANAGEMENT

(71) Applicant: GE Precision Healthcare LLC, Wauwatosa, WI (US)

(72) Inventors: Lu Jin, Jiangsu (CN); Qiang Yao, Jiangsu (CN); Dae Young Kim, Gyeonggi-do (KR); Bo Dan, Jiangsu (CN); Michael C. Macdonald, Wauwatosa, WI (US); Robert A. Meurer, Waukesha, WI (US); Todd E. Schueneman, Wauwatosa, WI (US); Ross Christopher Stalter, Waukesha, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 67 days.

(21) Appl. No.: 17/651,009

(22) Filed: Feb. 14, 2022

(65) Prior Publication Data

US 2023/0255592 A1    Aug. 17, 2023

(51) Int. Cl.
*A61B 8/00* (2006.01)

(52) U.S. Cl.
CPC .......... *A61B 8/4433* (2013.01); *A61B 8/4427* (2013.01); *A61B 8/4472* (2013.01); *A61B 8/56* (2013.01)

(58) Field of Classification Search
CPC ... A61B 8/4433; A61B 8/4427; A61B 8/4472; A61B 8/56
See application file for complete search history.

(56) References Cited

U.S. PATENT DOCUMENTS

| | | | |
|---|---|---|---|
| 5,673,696 A | 10/1997 | Bidwell et al. | |
| 10,895,751 B1* | 1/2021 | Yee | G02B 27/028 |
| 2009/0270727 A1* | 10/2009 | Zhao | A61B 8/4433 |
| | | | 248/305 |
| 2010/0249598 A1 | 9/2010 | Smith et al. | |
| 2011/0187323 A1* | 8/2011 | Gourley | H02J 7/0044 |
| | | | 320/111 |
| 2016/0317086 A1* | 11/2016 | Smith | H02J 50/10 |
| 2019/0380681 A1 | 12/2019 | Meurer et al. | |
| 2020/0254940 A1* | 8/2020 | Dang et al. | F16B 2/22 |
| 2023/0091876 A1* | 3/2023 | Carrillo | A63F 13/92 |
| | | | 320/108 |
| 2023/0225706 A1* | 7/2023 | Rahardja | A61B 8/4433 |
| | | | 600/437 |

FOREIGN PATENT DOCUMENTS

| | | | |
|---|---|---|---|
| CN | 204744242 U | | 11/2015 |
| KR | 20180034969 | * | 4/2018 |
| WO | 2008146207 A2 | | 12/2008 |

* cited by examiner

*Primary Examiner* — Alexei Bykhovski
(74) *Attorney, Agent, or Firm* — McCoy Russell LLP

(57) ABSTRACT

Various methods and systems are provided for ultrasound imaging probe power management. In one embodiment, a power management system for an ultrasound imaging system includes a wireless charger and a mount configured to couple to a probe holder of the ultrasound imaging system. The probe may seat against the wireless charger for charging of a power source of the probe.

19 Claims, 6 Drawing Sheets

METHODS AND SYSTEMS FOR ULTRASOUND PROBE POWER MANAGEMENT

TECHNICAL FIELD

Embodiments of the subject matter disclosed herein relate to ultrasound imaging, and more particularly, to probes for ultrasound imaging.

BACKGROUND AND SUMMARY

An ultrasound imaging system typically includes an ultrasound probe that is applied to a patient's body and a workstation or device that is operably coupled to the probe. The probe may be controlled by an operator of the system and is configured to transmit and receive ultrasound signals that are processed into an ultrasound image by the workstation or device. The workstation or device may show the ultrasound images through a display device. In some cases, wireless probes may be used to transmit data wirelessly to the ultrasound system, offering convenience and improved maneuverability for an operator of the probe.

Wireless ultrasound probes typically include power source, such as a rechargeable battery which demands regular recharging. In one previous example, the probe may be placed on a wireless charging base on a table, for instance, at a location spaced away from the system or workstation. The location or placement of the probe may be unsecured or unstable, in some cases, and may be inconvenient for operators of the ultrasound imaging system, which may lead to delays in use of the probe. As such, a charging arrangement which allows the probe to be charged at a more convenient location, nearer the workstation, may be desired.

To resolve at least some of the aforementioned issues, the inventors have developed a wireless charging assembly with a wireless charger configured to hold a rechargeable wireless ultrasound probe. The wireless charger is further configured to releasably couple to a mount that includes a quick-locking mechanism designed to allow the mount and wireless charger to be quickly and securely positioned in a probe holder formed in a workstation console. Further, the mount and the quick-locking mechanism thereof are designed to allow the mount to be coupled to a plurality of different probe holders having different shapes and/or sizes. In this way, the wireless charger may be quickly located, via the mount, near an ultrasound imaging system or workstation, so that the ultrasound probe may be conveniently charged at the workstation, greatly improving user experience and convenience.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIGS. 2-10 are shown approximately to scale, although other relative dimensions may be used, if desired.

DETAILED DESCRIPTION

The following description relates to various embodiments for ultrasound imaging probe power management. In one example, an ultrasound imaging system includes a wireless charger and a mount configured to couple to a probe holder of the ultrasound imaging system, where the wireless charger may be used for charging a wireless ultrasound imaging probe. As will be elaborated on herein, the mount may include a quick-locking member to provide easy and quick mounting of the wireless charger to the ultrasound imaging system at the probe holder (e.g., probe cup). The mount and wireless charger are couplable to probe holders having various different dimensions (e.g., size, shape, etc.) and are not limited to the probe holders described herein. Further, the wireless charger is easy to clean and has few moving parts or joints. Additionally, the wireless charger can be easily disassembled (e.g., for maintenance) and may be assembled with a relatively small assembly time.

By configuring the ultrasound imaging system to include the wireless charger and mount, a handheld ultrasound probe (e.g., wireless ultrasound probe) may be arranged more closely to the operator by seating the ultrasound probe against the wireless charger. As a result, an accessibility of the ultrasound probe may be increased. In some embodiments, the quick-locking member of the mount includes a biasing member (e.g., a compression spring or a torsion spring) and a slider or pivoting arm. The biasing member and the slider or arm may be manipulated by an operator so as to quickly engage and/or disengage the mount and wireless charger with the probe holder.

Figure 1:
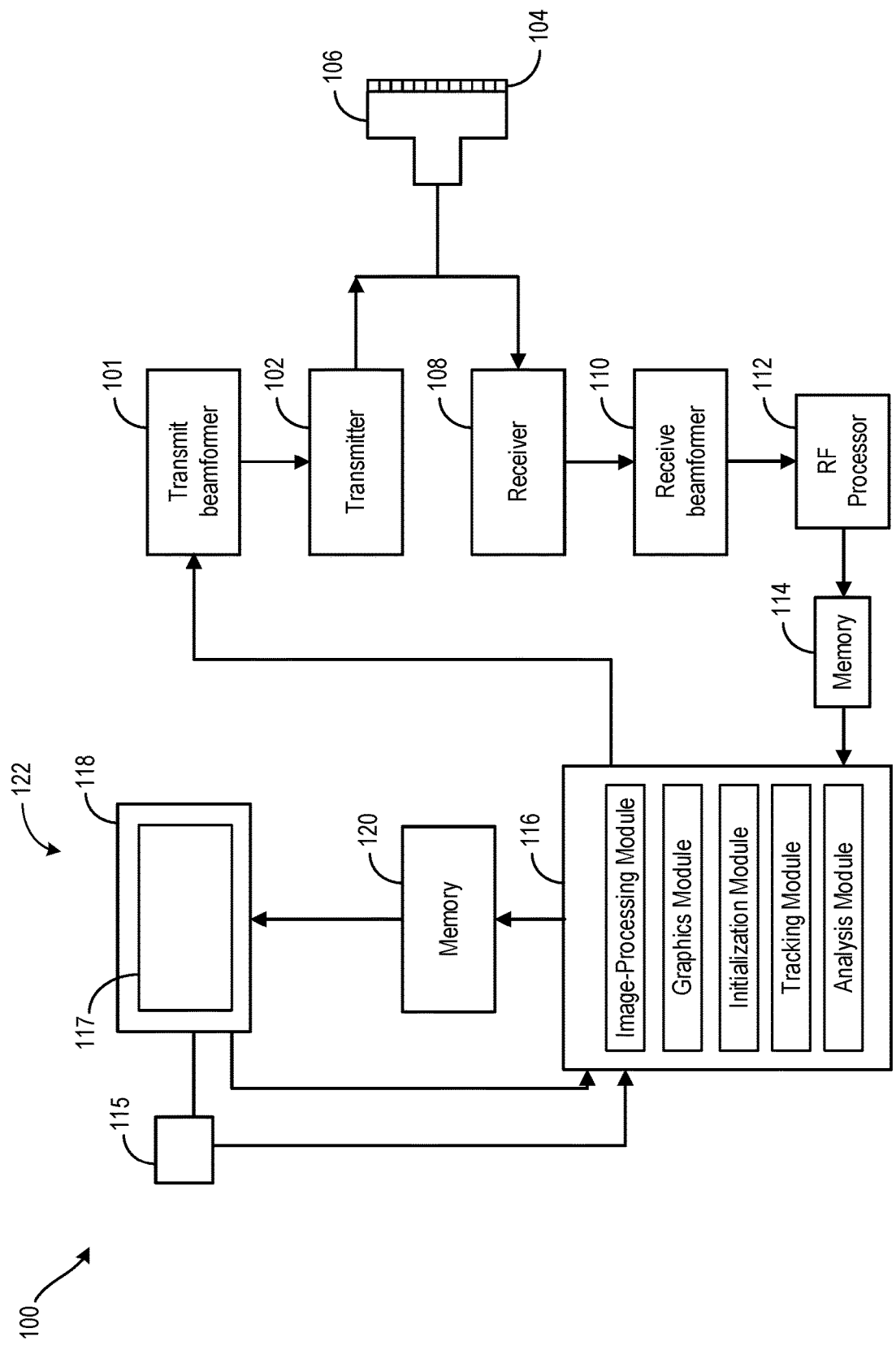
FIG. 1 schematically shows an ultrasound imaging system according to an embodiment of the disclosure.

FIG. 1 illustrates a block diagram of a system 100 according to one embodiment. In the illustrated embodiment, the system 100 is an imaging system and, more specifically, an ultrasound imaging system. As shown, the system 100 includes multiple components. The components may be coupled to one another to form a single structure in some examples. In some examples described herein, the system 100 may be a unitary system that is capable of being moved (e.g., portably) from room to room.

In the illustrated embodiment, the system 100 includes a transmit beamformer 101 and transmitter 102 that drives an array of elements 104 (e.g., piezoelectric crystals) within a diagnostic ultrasound probe 106 (or transducer) to emit pulsed ultrasonic signals into a body or volume (not shown) of a subject. The elements 104 and the probe 106 may have a variety of geometries. The ultrasonic signals are back-scattered from structures in the body, such as blood vessels and surrounding tissue, for instance, to produce echoes that return to the elements 104. The echoes are received by a receiver 108. The received echoes are provided to a receive beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage).

The system 100 also includes a system controller 116 that includes a plurality of modules, which may be part of a single processing unit (e.g., processor) or distributed across multiple processing units. The system controller 116 is configured to control operation of the system 100. For example, the system controller 116 may include an image-processing module that receives image data (e.g., ultrasound signals in the form of RF signal data or IQ data pairs) and processes image data. For example, the image-processing module may process the ultrasound signals to generate slices or frames of ultrasound information (e.g., ultrasound images) for displaying to the operator. The image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D). When multiple two-dimensional (2D) images are obtained, the image-processing module may also be configured to stabilize or register the images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium.

In operation, an ultrasound system may acquire data, for example, volumetric data sets by various techniques (for example, 3D scanning, real-time 3D imaging, volume scanning, 2D scanning with probes having positioning sensors, freehand scanning using a voxel correlation technique, scanning using 2D or matrix array probes, and the like). Ultrasound images of the system 100 may be generated from the acquired data (at the controller 116) and displayed to the operator or user on the display device 118.

The system controller 116 is operably connected to a user interface 122 that enables an operator to control at least some of the operations of the system 100. The user interface 122 may include hardware, firmware, software, or a combination thereof that enables an individual (e.g., an operator) to directly or indirectly control operation of the system 100 and the various components thereof. As shown, the user interface 122 includes a display device 118 having a display area 117. The display device 118 may be a touchscreen display that enables the operator to adjust operating parameters of the system 100 by directly interacting with (e.g., touching) the display device 118. For example, the display device 118 may be configured such that when a user moves a finger/glove/stylus across the face of the display device 118, a cursor atop the ultrasound image on the display area 117 moves in a corresponding manner. The display device 118 may detect a presence of a touch from the operator on the display area 117 and may also identify a location of the touch in the display area 117. The touch may be applied by, for example, at least one of an individual's hand, glove, stylus, or the like. As such, the touch-sensitive display may also be characterized as an input device that is configured to receive inputs from the operator. The display device 118 also communicates information from the controller 116 to the operator by displaying the information to the operator. The display device 118 and/or the user interface 122 may also communicative audibly. The display device 118 is configured to present information to the operator during the imaging session. The information presented may include ultrasound images, graphical elements, user-selectable elements, and other information (e.g., administrative information, personal information of the patient, and the like). In some embodiments, the user interface 122 may be additionally configured to interface with (e.g., electronically couple to) one or more user interface input devices 115, such as a physical keyboard, mouse, and/or touchpad.

In addition to the image-processing module, the system controller 116 may also include a graphics module, an initialization module, a tracking module, and an analysis module. The image-processing module, the graphics module, the initialization module, the tracking module, and the analysis module may coordinate with one another to present information to the operator during and/or after the imaging session. For example, the image-processing module may be configured to display an acquired image on the display device 118, and the graphics module may be configured to display designated graphics along with the ultrasound image, such as graphical outlines, which represent lumens or vessel walls in the acquired image. The image-processing and/or graphics modules within the system controller 116, may also be configured to generate a 3D rendering or image (not shown) of the entire vascular structure.

In some embodiments, the system controller 116 may also house an image-recognition module (not shown), which accesses stored images/videos (i.e., an image library) from either or both of the memory 114 and the memory 120, before analyzing them. For example, knowing the parameters under which a protocol is being carried out (ultrasound type, scan plane, tissue being imaged, etc.) the image recognition module may compare a live image on the display area 117, to one stored in memory 120, in order to analyze the image and thereby improve the accuracy of placing and utilizing analytical tools. In an alternative embodiment, instead of utilizing an image recognition module and image library, the system controller may house instructions for analyzing acquired imaging data (e.g., ultrasound images/videos acquired with the probe) and automatically determining a desired placement of one or more analytical tools, such as a region of interest.

The screen of the display area 117 of the display device 118 is made up of a series of pixels which display the data acquired with the probe 106. The acquired data includes one or more imaging parameters calculated for each pixel, or group of pixels (for example, a group of pixels assigned the same parameter value), of the display, where the one or more calculated image parameters includes one or more of an intensity, velocity, color flow velocity, texture, graininess, contractility, deformation, and rate of deformation value. The series of pixels then make up the displayed image generated from the acquired ultrasound data.

As shown by FIGS. 2-10, an ultrasound imaging system, such as the ultrasound imaging system 100 shown by FIG. 1 and described above, includes a wireless charger and a mount configured to couple to a probe holder of the ultrasound imaging system, where the wireless charger can be used for charging a wireless ultrasound imaging probe in a more convenient location compared previous probe charging configurations. As will be elaborated on herein, the mount may include a quick-locking member to provide easy and quick mounting of the wireless charger to the ultrasound imaging system at the probe holder (e.g., probe cup). The mount and wireless charger are couplable to probe holders having various different dimensions (e.g., size, shape, etc.) and are not limited to the probe holders described herein. The wireless charger is easy to clean and has few moving parts or joints. Additionally, the wireless charger can be easily disassembled (e.g., for maintenance) and may be assembled with a relatively small assembly time. By configuring the ultrasound imaging system to include the wireless charger and mount, a handheld ultrasound probe (e.g., wireless ultrasound probe) may be arranged more closely to the operator by seating the ultrasound probe against the wireless charger. As a result, an accessibility of the ultrasound probe may be increased.

A first exemplary embodiment of a wireless charger and mount is depicted in FIGS. 2-7. An axis system 201 is provided in FIGS. 2-4, and another axis system 501 is provided in FIGS. 5-7, for reference. The z-axis may be a vertical axis (e.g., parallel to a gravitational axis), the x-axis may be a lateral axis (e.g., a horizontal axis), and the y-axis may be a longitudinal axis, in one example. However, the axes may have other orientations in other examples.

Figure 2:
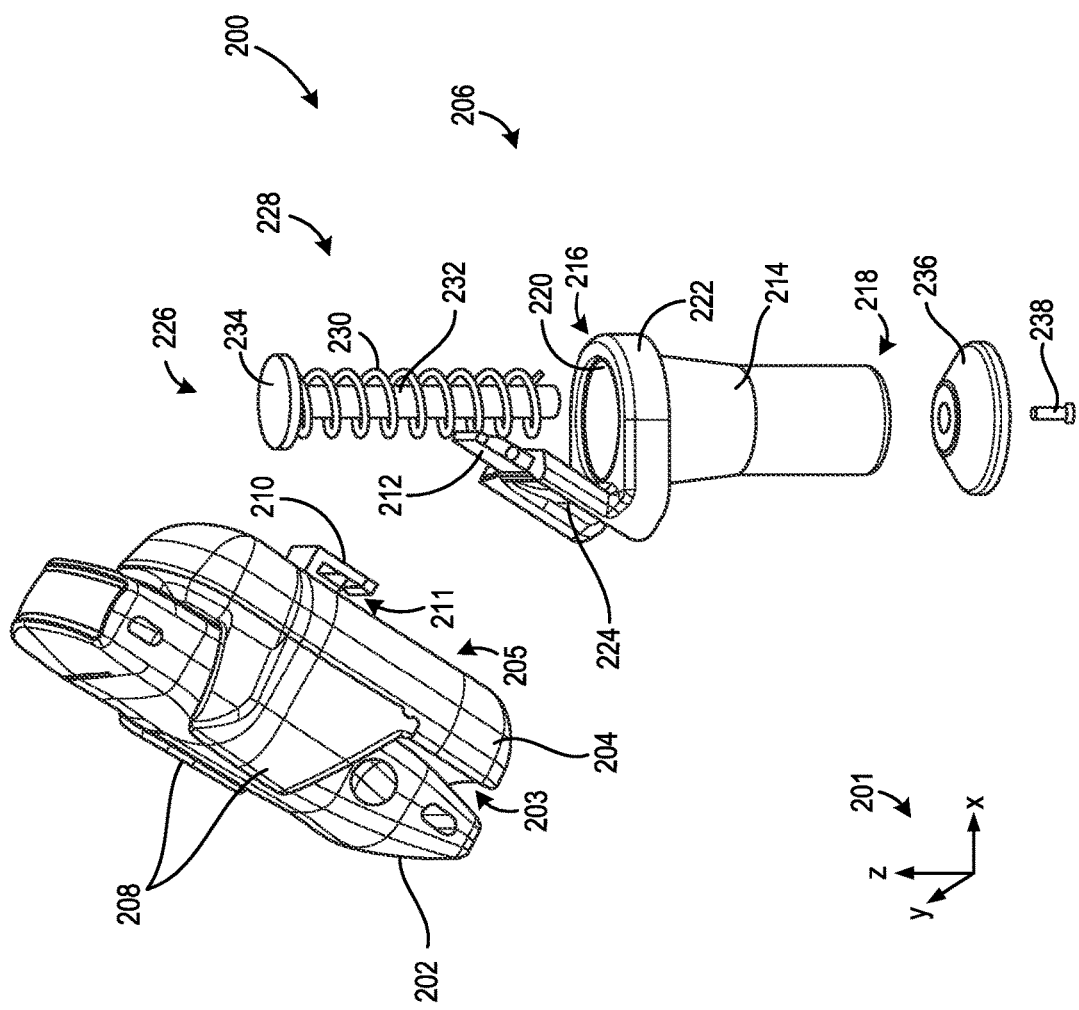
FIG. 2 shows a view of wireless charger and mount for a probe of an ultrasound imaging system in a decoupled configuration according to an embodiment of the disclosure.

Turning now to FIG. 2, a wireless charger and mount assembly 200 for a wireless ultrasound imaging probe 202 is shown, according to the first exemplary embodiment of the disclosure. The assembly 200 includes a wireless charger 204 and a mount 206. In one example, the wireless charger 204 may be fixed (e.g., mounted) to the mount 206. Further, the probe 202 may be seated against the wireless charger 204 of the assembly 200. More specifically, the probe 202 may be positioned along a first major surface 203 (e.g., an upper surface) of the wireless charger 204 opposite a second surface 205 (e.g., a lower surface) of the wireless charger. Further, in some examples, the wireless charger 204 may include a pair of arms 208 extending outward from opposing sides of the first major surface 203 of the wireless charger for retaining the probe 202 thereon. The arms 208 may be integrally formed with a body (e.g., housing) of the wireless charger 204, in some cases, and may be formed of a flexible (e.g., resilient) material so that the arms can be positioned at least partially around a portion of the probe 202 (e.g., so as to retain the probe 202 on the wireless charger). In other examples, however, other mechanisms for retaining the probe on the wireless charger have been contemplated, such as providing a textured surface on the first major surface of the charger, for instance, for gripping a surface of the probe that is positioned thereon.

The wireless charger 204 may further include a clip 210 formed on the second surface 205 thereof configured to interface with a corresponding feature (e.g., tab 212) on the mount 206. To elaborate, the mount 206 may include an elongated hollow post 214 having a generally cylindrical structure. The hollow post 214 includes openings at an upper end 216 and a lower end 218 thereof, such that an inner wall 220 defines a bore extending through the hollow post (between the upper and lower ends 216, 218). The bore defined by the inner wall 220 may thus open at the upper and lower ends of the hollow post 214.

The post 214 further includes a rim 222 formed at the upper end 216. The rim 222 may further include an extension 224 that extends outward (e.g., generally upward) from the rim 222 and terminates in a tab 212. In one example, the tab 212 may be shaped and sized so as to fit within a slot 211 defined between the clip 210 and the second surface 205 of the wireless charger 204. Thus, the wireless charger 204 may be positioned on the post 214 of the mount 206 by aligning the clip 210 with the extension 224 and sliding the clip 210 over the tab 212 so as to releasably secure the wireless charger on the mount (as shown in an assembled configuration of the assembly 200 in FIGS. 3-4). In this way, an operator may easily and quickly secure (e.g., latch) the wireless charger 204 to the mount 206. In some examples, the clip 210 and/or the tab 212 may be formed with additional features (e.g., one or more protrusions and/or indentations) so as to provide a snap-fit latching connection, which may provide an even more secure coupling between the wireless charger 204 on the mount 206, while still allowing an operator to easily and quickly couple and decouple the wireless charger therefrom, as desired.

As previously mentioned, the wireless charger and mount assembly 200 further includes a quick-locking mechanism for coupling the mount 206 (and therefore the wireless charger 204, as desired) to a probe holder of an ultrasound system. To elaborate, the mount 206 may further include a locking (e.g., quick-locking) member 226 that includes a slider 228 and a biasing member 230 (e.g., spring). Specifically, the slider 228 may include a shaft 232 with a head 234 formed at an upper end thereof, where a diameter of the head 234 is greater than a diameter of the shaft 232. Further, the biasing member 230 may be a compression spring disposed about the shaft 232, such that an upper end of the spring 230 is adjacent to a bottom side of the head 234. Even further, when the slider 228 and the spring 230 are assembled with the mount 206 (e.g., within the hollow post 214), as will be discussed in detail with regard to FIGS. 3-4, a base 236 is attached to a lower end of the shaft 232 of the slider by a fastener, such as a screw 238, for instance.

Figure 3:
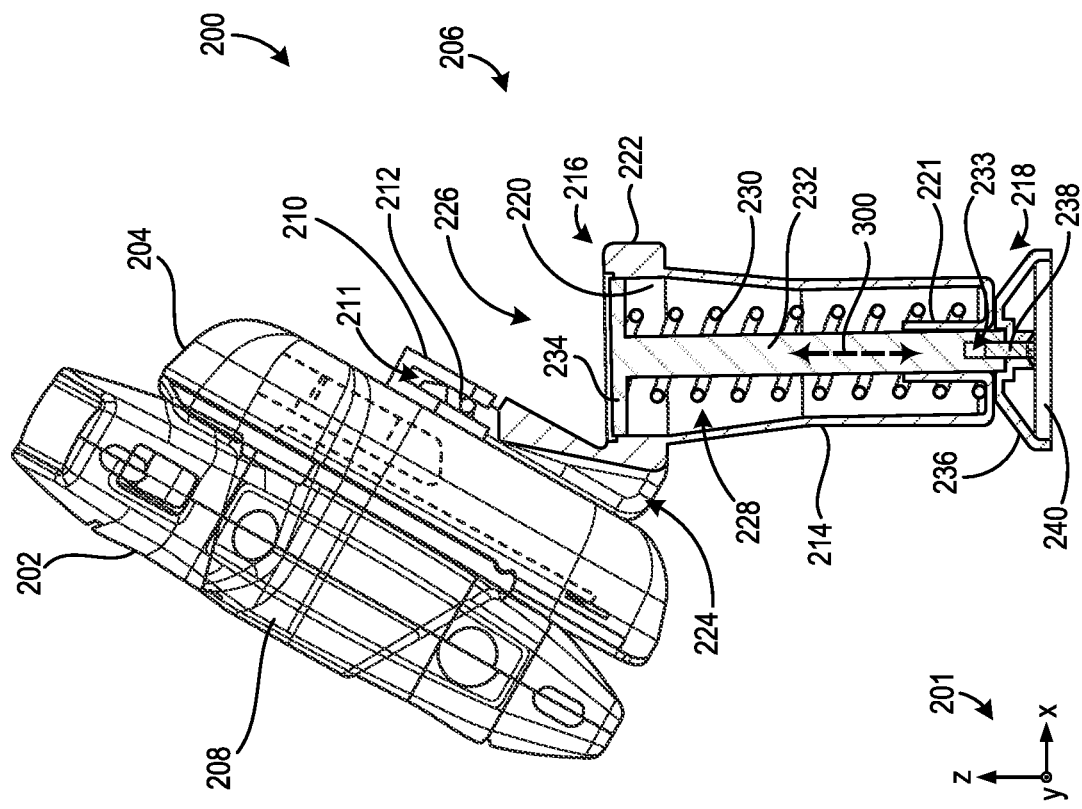

Turning to FIG. 3, the assembled configuration of the wireless charger and mount assembly 200 is shown, particularly illustrating the wireless charger 204 and the locking member 226 assembled with the mount 206. As shown, the wireless charger 204 is coupled with the mount 206 via the interface between the clip 210 and the tab 212 on the extension 224 of the mount 206. Further, the locking member 226 may be at least partially disposed within the hollow post 214. In one example, the hollow post 214 may be formed so that the inner wall turns inward near the lower end 218 to form a guide portion 221 within the post for receiving a lower end of the shaft 232 of the slider 228. Thus, the slider 228 may extend through the opening formed by the guide portion 221 of the hollow post 214 (at the lower end 218 of the hollow post), such that the base 236 may be coupled to the shaft 232 (at a bottom end thereof) via a screw 238. Additionally, in some examples, a cover 240 may be coupled with the base 236 and covering the screw 238.

Thus, the base 236 and/or the cover 240 may form a grip or handle of the locking member 226, operable by a user to move the slider 228 axially through the hollow post 214 of the mount 206. In an initial resting position, as illustrated in FIG. 3, the slider 228 is positioned within the hollow post 214. The spring 230 is positioned about the shaft 232, having an upper end abutting the head 234 (e.g., near the upper end 216 of the hollow post) and a lower end engaging the guide portion 221 of the hollow post 214 (e.g., near the lower end 218 of the hollow post). Thus, the spring 230 may exert a biasing force that urges the shaft 232 and the base 236 in an upward direction along a main axis 300 of the mount 206 (depicted in FIG. 3), where the lower end 218 of the hollow post 214 acts as a stop for the base 236.

Figure 4:
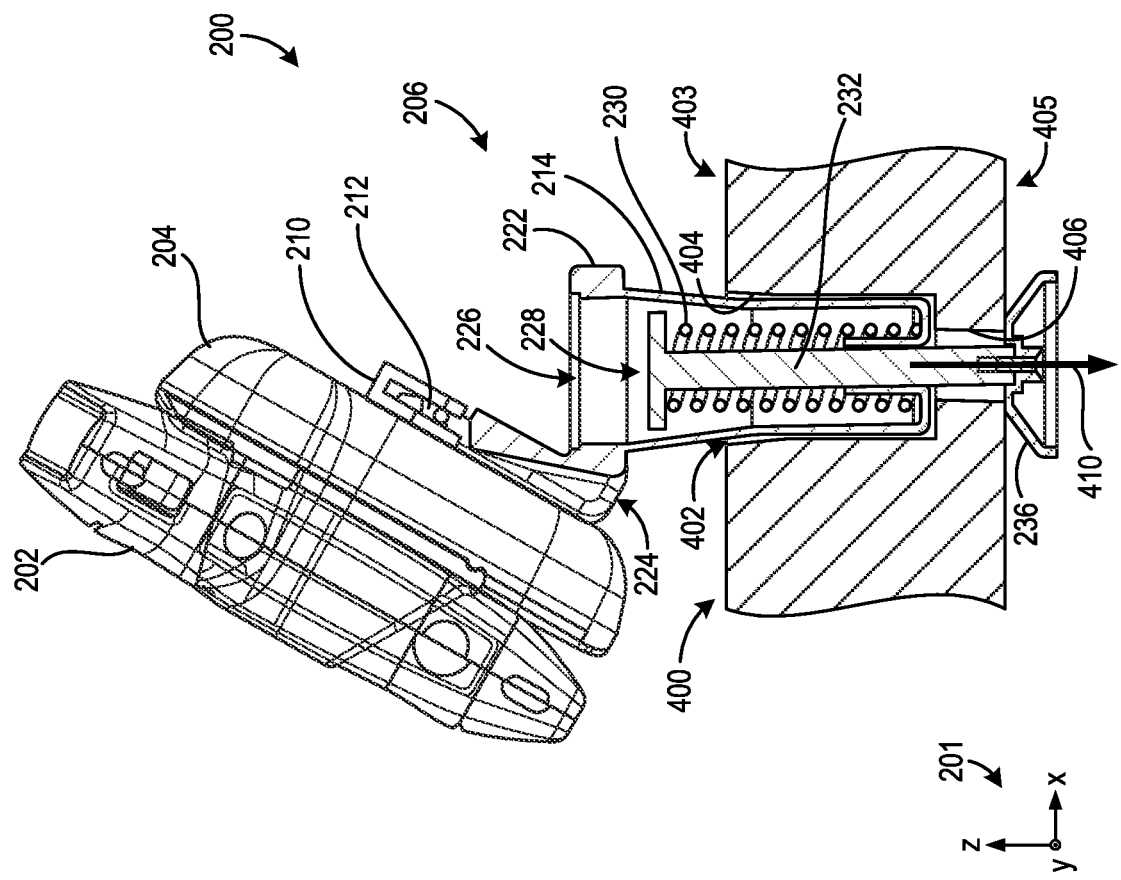
FIGS. 3 and 4 show side views of the wireless charger and mount in a coupled configuration, particularly illustrating a cross-sectional view of the mount, with FIG. 4 showing the wireless charger and mount coupled with a holder.

FIG. 4 illustrates the wireless charger and mount assembly 200 positioned in, and coupled to a holder in a structure 400. The structure 400 may be a section of an ultrasound imaging system workstation or device, such as a probe holder or other device holder designed for holding any of a variety of imaging probes or other tools and implements, in some examples, as will be elaborated on with regard to FIGS. 5-7. In other examples, however, the structure 400 may be any other structure or housing having an opening 402 shaped and sized for receiving the mount 206.

In the example shown in FIG. 4, the structure 400 includes the opening 402 extending between a top surface 403 and a bottom surface 405 of the structure. Further, the opening 402 may include a first upper section 404 extending from the top surface 403 and in communication with a second, lower section 406 extending from the bottom surface 405. The upper section 404 may be sized to accommodate the hollow post 214 of the mount 206 and may, in some examples, have a diameter wider than a diameter of the lower section 406. The lower section 406 may be sized to accommodate a portion of the slider 228, when the slider 228 is moved downwards within the hollow post 214 (e.g., compressing the spring 230). When the hollow post 214 of the mount 206 is positioned within the upper section 404 of the opening and the slider 228 is moved downward, in the direction shown by arrow 410, the base 236 (attached to the lower end of the slider 228) is positioned adjacent to the bottom surface 405 of the structure 400, Further, the spring 230 urges the base 236 towards the bottom surface of the structure upon removal of a force on the slider (e.g., by an operator) in the direction of arrow 410, such that the mount 206 is automatically locked within the opening 402 of the structure 400. Thus, a wireless charger 204 for charging a probe 202 may be securely coupled with a reliable, quick-coupling device adaptable for use with a variety of holders or openings, such as the opening 402 in the surface 402, having a variety of different shapes and sizes and implemented in different structures, housings and/or environments. Further, while the probe 202 disclosed herein is described as a wireless ultrasound imaging probe, and more generally as a rechargeable device configured to wirelessly interface with the wireless charger 204, it will be understood that the probe 202 may be any device capable of being charged by the wireless charger 204, and the wireless charger may be shaped and sized accordingly, in different examples. Details of placing (e.g., positioning) the mount within an opening, such as a probe holder, will be elaborated on with regard to FIGS. 5-7.

Figure 5:
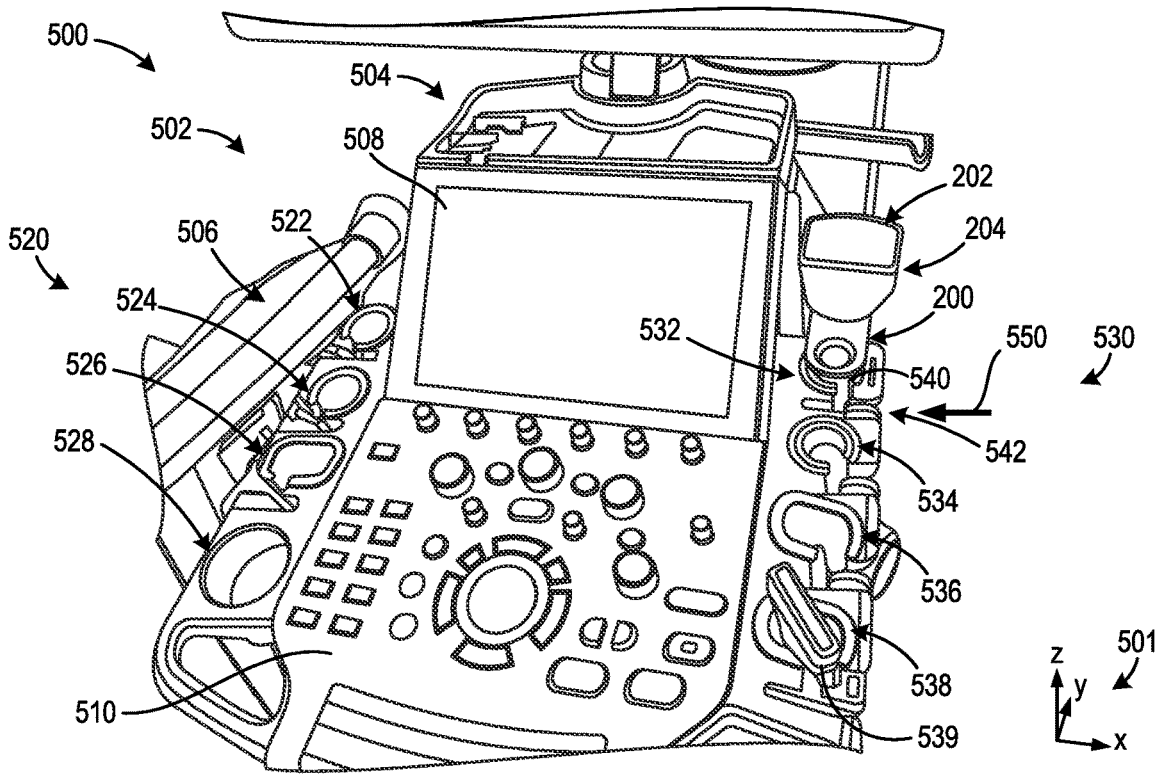
FIG. 5 shows the wireless charger and mount in the coupled configuration with a probe holder of the ultrasound imaging system.

One exemplary ultrasound imaging system 500 according to the disclosure herein is shown in FIG. 5. The ultrasound imaging system 500 may include a portable ultrasound system 502 (e.g., a portable device or workstation). In one example, the portable ultrasound system 502 may be similar to the system 100 described above with reference to FIG. 1. Thus, the portable ultrasound system 502 may be a unitary system that is capable of being separated (e.g., decoupled) from a remainder of the ultrasound imaging system 500 and may be moved (e.g., portably) from room to room relative to the remainder of the ultrasound imaging system 500, which may stay in place and/or be moved with the portable ultrasound system 502. The portable ultrasound system may include several components similar to those described above with reference to the system 100 (e.g., similar to the display device 118, memory 120, system controller 116, probe 106, transmitter 102, receiver 108, etc.). The portable ultrasound system 502, and particularly a method for coupling the wireless charger and mount assembly 200 thereto, will be described in further detail below with reference to FIGS. 5-7.

As shown in FIG. 5, the portable ultrasound imaging system 502 may include a support stand, generally indicated at 504, that may carry various trays, storage containers, etc., for various system devices and/or accessories (e.g., fluid containers, disinfectants, etc.). The system may further include casters (not shown) for supporting the support stand 504 in addition to a and may further include casters (not shown) configured to support the support stand 504 against a ground surface (not shown) and to enable the support stand to more easily move across the ground surface (e.g., roll along the ground surface). The z-axis of references axes 501 is an axis positioned vertical relative to the ground surface (e.g., extending in a vertical, normal direction relative to the ground surface).

The portable system 502 may further include a user interface system 506 carried by the support stand 504. The user interface system 506 may include a display device 508 (e.g., similar to display device 118 of FIG. 1) for displaying ultrasound images of the system 500 generated from acquired data to an operator or user. In some examples, the display device 508 may be a touch-sensitive graphical display, also referred to as a touchscreen, that enables the operator to adjust operating parameters of the system 500 by directly interacting with (e.g., touching) the display device 508. Additionally or alternatively, the user interface system 506 may further include a user input device panel 510 including various input devices (e.g., keys (of a keyboard), buttons, knobs, switches, etc.) that enable an operator to adjust operating parameters of the system 500 and/or display parameters for images displayed on the display device 508.

The portable system 502 further includes one or more storage sections, such as storage sections 520, 530 shown on opposite sides of the user interface system 506. The storage sections each include a plurality of openings configured as probe holders. For example, the storage section 520 may include four probe holders 522, 524, 526, 528, and the storage section 530 may include four probe holders 532, 534, 536, 538, as illustrated, though other numbers of probe holders in each section have been contemplated, in different examples. Each of the probe holders may include an opening extending between a top surface and a bottom surface of the respective storage section. For instance, the probe holders may include an opening similar to the opening 402 shown in FIG. 4, extending from the top surface 403 to the bottom surface 405 of a structure 400, such that the opening further includes an upper section having a diameter greater than a diameter of a lower section.

Returning to FIG. 5, each of the probe holders in the storage sections 520, 530 includes an opening (which may or may not be similar to the opening 402) that is shaped and sized to receive an ultrasound probe or other device. In one particular example according to the present disclosure, the opening of the probe holder may be configured (e.g., shaped and sized) to receive a wireless charger (for an ultrasound probe or other rechargeable device) and a mount assembly. For example, the probe holder 532 includes an opening 540 which may receive the wireless charger and mount assembly 200 described above. The probe holder 532 is further illustrated including a slot 542 which extends between the opening 540 and an exterior surface of the storage section 530 (e.g., a laterally exterior side of the storage section). The slot 542 enables the assembly 200 (and particularly the mount thereof) to be inserted through the gap formed by the slot 542 (e.g., in the direction of arrow 550) such that at least a portion of the assembly is positioned within the opening 540. Assembly configurations for coupling the wireless charger and mount assembly 200 within a probe holder (e.g., the probe holder 532) of a storage section on the portable ultrasound system will be further described and illustrated with respect to FIGS. 6-7.

Although the assembly 200 is depicted as being coupled with the probe holder 532 in FIG. 5, it will be understood any of the probe holders 522-528 and 532-538 may include an opening (extending between the top and bottom surfaces of the respective storage section) configured for holding a wireless charger and mount assembly, as described herein, or an ultrasound probe (e.g., as shown by probe 539 held in probe holder 538 in FIG. 5). Each of the probe holders may also include a slot (extending between the top and bottom surfaces of the respective storage section) the connects the opening to a lateral exterior surface of the storage section so that the probe or other device (e.g., mount for the wireless charger) may be inserted through the slot and positioned in the respective opening. In some examples, the storage sections 520, 530 may include a different number of openings and/or slots. Further, the openings and/or slots of the probe holders in the storage sections 520, 530 may have different shapes and/or sizes, for accommodating various probes and other devices having different shapes and/or sizes. For instance, the opening may have a circular shape (e.g., a circular cross-section taken in the x-y plane), as illustrated with probe holders 522, 526, 528, 540, and 534, or a rounded rectangular shape (e.g., cross-section taken in the x-y plane), as illustrated in probe holders 526, 536, and 538. The wireless charger and mount assembly described herein may be capable of coupling with a plurality of different probe holder shapes and/or sizes, such that the locking mechanism may adaptably couple the mount within different openings, as desired.

Figure 6:
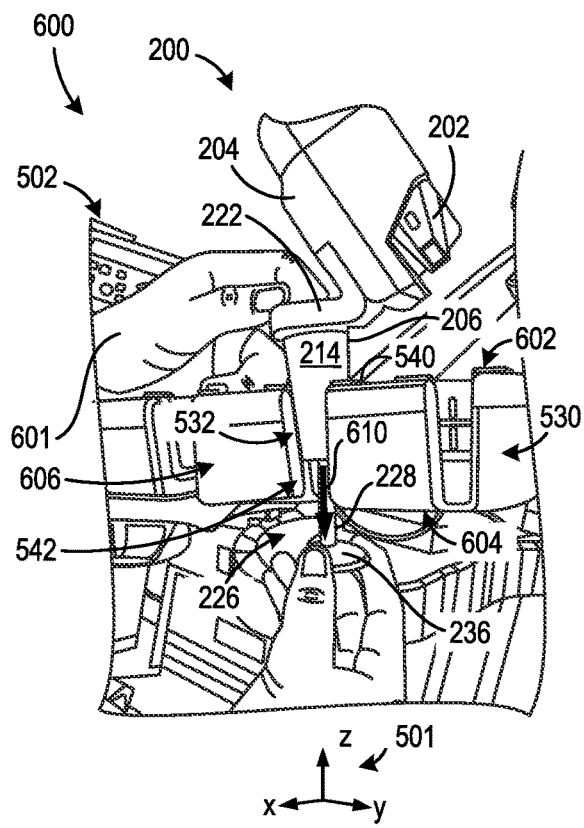
FIG. 6 shows a first arrangement of the wireless charger and mount in a sequence of coupling to the probe holder of the ultrasound imaging system.
Figure 7:
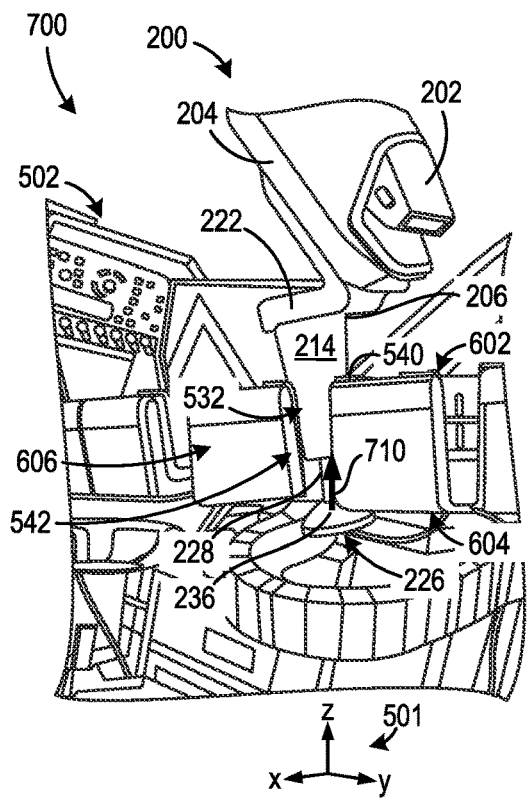
FIG. 7 shows a second arrangement of the wireless charger and mount in the sequence of coupling to the probe holder of the ultrasound imaging system.

First and second assembly configurations for coupling the wireless charger and mount assembly 200 within a probe holder of the portable ultrasound system 502 are described with respect to FIGS. 6 and 7, respectively. In these configurations, the wireless ultrasound probe 202 rests on the wireless charger 204, and the wireless charger 204 is releasably coupled with the mount 206 (e.g., at the rim 222 of the hollow post 214), as previously described with respect to FIGS. 2-4.

Referring now to FIG. 6, in a first assembly configuration 600, an operator 601 may use one hand to grip the mount 206 at an upper end thereof (e.g., by holding the rim 222 of the hollow post 214) and use the other hand to grip the base 236 (attached to the slider 228 of the locking member 226. The operator 601 may then pull the slider downwards, as shown in the direction of arrow 610, thereby moving slider 228 of the locking member 226 relative to the hollow post 214 of the mount 206. In this way, the biasing member is compressed within the hollow post 214 of the mount 206 (e.g., as shown in FIG. 4 when compression spring 230 is compressed by movement of the slider 228 in the direction of arrow 410 shown in FIG. 4) and a portion of the slider 228 is moved to extend out from a bottom end of the hollow post 214, as illustrated in FIG. 6.

The operator 601 may then insert the slider 228 and/or the hollow post 214 of the mount 206 through the slot 542 formed in the storage section 530 of the portable ultrasound system (e.g., by moving the assembly in the direction of arrow 550 shown in FIG. 5). To elaborate, the slot 542 of the probe holder 532 is formed in an external side surface 606 (e.g., a generally vertically oriented side surface) of the storage section 530. Further, the slot 542 extends from a top surface 602 of the storage section and a bottom surface 604 of the storage section, where the side surface 606 spans between the top and bottom surfaces. Even further, as previously mentioned, the slot 542 defines a passage between the side surface 606 and the opening 540 of the probe holder, which opening 540 also extends between the top surface 602 and the bottom surface 604 of the storage section 530. Thus, by inserting the mount 206 through the slot 542, with the slider 228 moved (e.g., by the operator 601) into the extended position shown in the first assembly configuration 600, the mount 206 may be easily and quickly positioned within the opening 540 of the probe holder 532.

Next, turning to the second assembly configuration 700 shown in FIG. 7, the operator releases the slider 228 of the locking member 226 upon positioning the mount 206 of the assembly 200 in the opening 540 of the probe holder 532. Upon removing the force applied by the operator to the slider 228, the biasing member (e.g., spring 230 shown in FIGS. 2-4) urges the sliding member in the direction of arrow 710 (e.g., upwards, in a direction opposite the direction of arrow 610 shown in FIG. 6). Therefore, the base 236 attached at the bottom end of slider 228 is pressed against the bottom surface 604 of the storage section 530, while the weight of the probe 202 and wireless charger 204 coupled to the mount 206 assist in maintaining the position of the assembly 200 with respect to the probe holder 532.

In this way, the locking member 226 enables the wireless charger and mount assembly 200 to be automatically secured (e.g., locked) into position within the probe holder 532, as desired. Further, to decouple the wireless charger and mount assembly 200 from the probe holder, the base 236 and slider 228 may be moved away from the hollow post 214 (similar to the configuration shown in FIG. 6) so that the mount 206 can be unseated from the opening 540 of the probe holder 532 and moved laterally outward from the probe holder through the slot 542. Thus, the wireless charger 204 may be quickly positioned (or repositioned) in a convenient location proximate the portable ultrasound system 502, as desired, thereby allowing the ultrasound probe 202 to be quickly and easily charged as demanded by coupling and decoupling the probe from the assembly 200.

Figure 9:
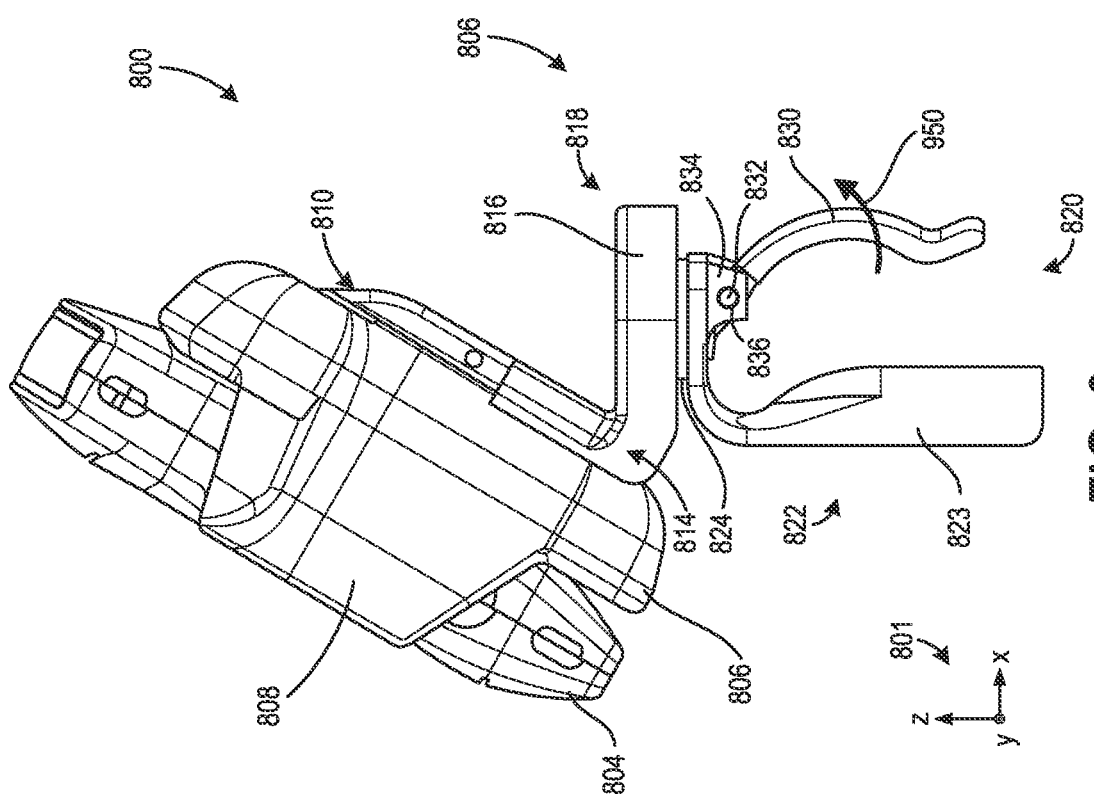
FIG. 9 shows the mount and wireless charger of FIG. 8 in an assembled configuration.
Figure 8:
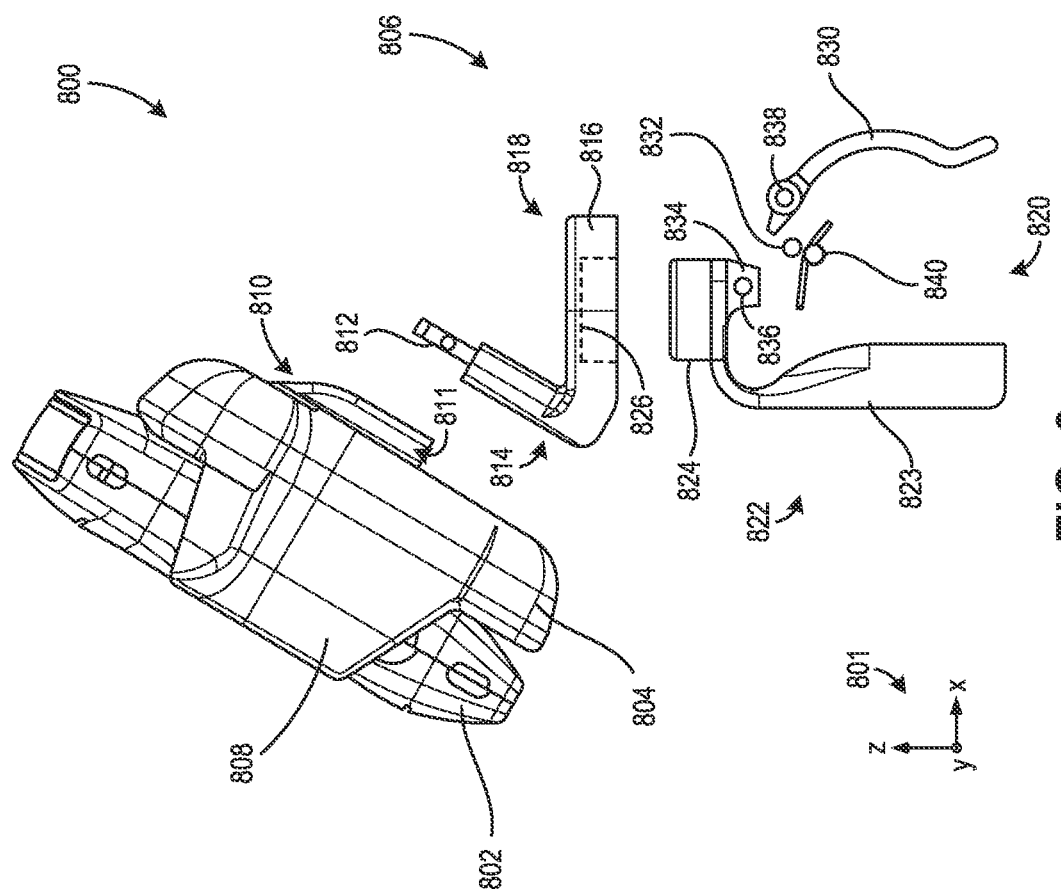
FIG. 8 shows another mount and wireless charger for a probe of an ultrasound imaging system, in a disassembled configuration, according to an embodiment of the disclosure.
Figure 10:
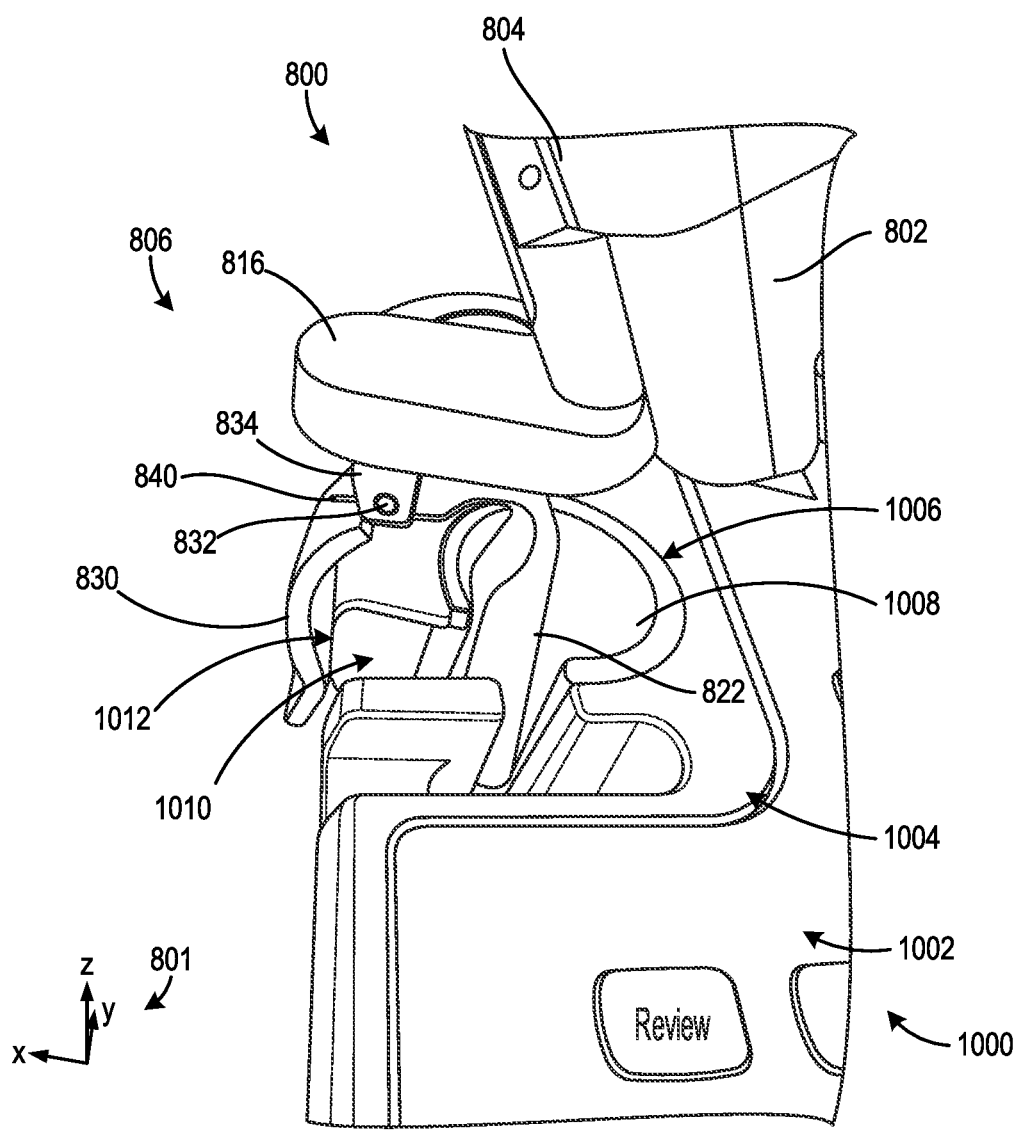
FIG. 10 shows an arrangement of the wireless charger and mount of FIGS. 8-9 coupled to the probe holder of the ultrasound imaging system.

Another exemplary embodiment of a wireless charger and mount assembly 800 for an ultrasound imaging probe 802 is shown in FIGS. 8-10. An axis system 801 is provided in FIGS. 8-10, for reference. The z-axis may be a vertical axis (e.g., parallel to a gravitational axis), the x-axis may be a lateral axis (e.g., a horizontal axis), and the y-axis may be a longitudinal axis, in one example. The assembly 800 includes a wireless charger 804 and a mount 806. The probe 802 may be seated against the wireless charger 804. Further, the probe 802 and the charger 804 may share substantial similarities with the probe 202 and the wireless charger 204 described with respect to FIGS. 2-7. For instance, the wireless charger 804 may include a pair of arms 808 extending outwardly from a major surface thereof and configured for retaining (e.g., gripping) the probe 802 in the configuration shown in FIGS. 9-10. Repeated discussion of the releasable coupling between the probe 802 and the wireless charger 804 will be omitted for brevity.

The wireless charger 804 may be releasably fixed (e.g., mounted) to the mount 806, as shown in the assembled configuration depicted in FIG. 9. In one particular example, the mount 806 may be constructed from multiple parts, including a base 816 configured to releasably couple with the wireless charger 804. The base 816 may be disposed near an upper end 818 of the mount 806, opposite a lower end 820 of the mount. Further, the base 816 may include an extension 814 extending upward from the base and including a tab 812 configured for engaging a slot 811 formed by a clip 810 formed on the wireless charger 804. Thus, the base 816, extension 814 and tab 812 may be substantially similar to the rim 222, extension 224 and tab 212 described with respect to FIGS. 2-4 (for releasably coupling with the clip 210 formed on the wireless charger 204) and further discussion of the coupling between the wireless charger 804 and the base 816 of the mount 806 will be omitted for brevity.

The mount 806 may further include a post 822 coupled with the base 816. In one example, the post 822 may include an elongated, generally cylindrical portion 823 that extends below the base 816 (which is positioned at the upper end 818 of the mount 806). Further, the post 822 may include protrusion 824 disposed above the elongated portion 823. The protrusion 824 may be shaped and sized so as to fit within a corresponding recess 826 formed in a bottom side of the base 816, so that the base 816 may be positioned on (e.g., coupled to) the post 822. For example, the recess 826 may extend vertically through a portion the base 816, and the protrusion 824 may be shaped and sized so as to be inserted in the recess 826 to releasably couple the base 816 with the post 822. In other examples, the recess 826 may instead be formed as an aperture, extending through the base 816 from a top side to a bottom side thereof. Other coupling arrangements between the base 816 and the post 822 have been contemplated, in different examples. Alternatively, the base 816 and the post 822 may be integrally formed (e.g., as a unitary structure), in some examples.

The mount 806 further includes a locking clip 830 pivotally coupled to the post 822 via a rotation shaft 832. To elaborate, the post 822 may include one or more extensions or tabs 834 positioned below the protrusion 824 located near an upper end of the mount 806. An aperture 836 is formed in each of the one or more extensions 834, where the apertures are sized and arranged (e.g., aligned) to enable the rotation shaft 832 to be inserted therethrough. A corresponding aperture 838 is formed in an upper end of the locking clip 830, such that when the locking clip 830 is assembled with the post 822, as shown in the assembled view of the mount 806 in FIG. 9, the apertures 836, 838 are aligned and the rotation shaft 832 inserted through the apertures provide the pivotal coupling between the locking clip 830 and the post 822.

In one example, the mount 806 further includes a biasing member 840, such as a torsion spring 840 positioned between the locking clip 830 and the post 822. Specifically, the spring 840 may be arranged around the rotation shaft 832 and configured to bias the locking clip 830 towards the post 822. In order to couple the assembled wireless charger and mount assembly 800, shown in FIG. 9, within a probe holder on a portable ultrasound system, an operator may move the locking clip 830 in the direction of arrow 950 (e.g., pivot the locking clip about the rotation shaft 832 in the direction of arrow 950), against a biasing force exerted by the spring 840. An assembly configuration showing the wireless charger and mount assembly 800 coupled with a probe holder will be described with respect to FIG. 10.

In some examples, additionally or alternatively, the mount may be modified to operate in a variety of disparate settings. For example, the mount may be configured to couple to a post or a pole. The mount may include a hollow tube sealed at one end and open at an opposite end. The open end may be configured to receive the post and the closed end may be configured to couple to the wireless charge and mount assembly for the ultrasound probe. The mount may include one or more elements configured to engaged with the post to militate separation therefrom. The one or more elements may include clamps, protrusions, threading, a resilient member, or other locking element.

In another embodiment, additionally or alternatively, the mount may be configured to couple to the post or pole via a hollow tube. The hollow tube may be open at both extreme ends. The hollow tube may further include an opening, such as a slit, extending from the open extreme ends. The slit may provide a degree of flexibility for the hollow tube to open and couple to the post. In one example, a sizing, such as a diameter, of the hollow tube may correspond to a diameter of the post. In one example, the diameter of the hollow tube may be oversized to fit larger posts. One or more adapters may be inserted into the hollow tube to allow the hollow tube to couple to smaller posts. The wireless charger for the ultrasound probe and mount system may couple to the mount along a longitudinal section of the hollow tube opposite the slit.

In a further embodiment, additionally or alternatively, the mount may be configured to as a clip. The clip may be shaped to couple to a table, a tray, or other planar surface. The clip may include one or more features configured to provide counterforces by contacting a surface to maintain the wireless charger, the ultrasound probe, and the mount system level. Level may include where the ultrasound probe is in an upright position or a substantially upright position (e.g., ±10 degrees of 90 relative to the surface). In one example, the clip may include a C-shape, a J-shape, a U-shape, or other similar shape. The opposite ends of the clip may provide an upward force and a downward force against the surface to maintain level. The clip may be further customized to engaged with different shapes of tables and trays.

In other embodiments, additionally or alternatively, the mount may be shaped to couple to a holster. Additionally or alternatively, the mount may engage with vest, a belt, or other similar apparel device. In this way, the mount may be configured to couple the wireless charger, the ultrasound probe, and the mount system to a variety of different elements. The elements may be arranged in stationary settings or mobile settings, wherein the mount may be configured to adjust a coupling force to reduce a likelihood of separation between the mount and the element to which it is coupled.

FIG. 10 depicts a portion of a portable ultrasound system 1002 of an ultrasound imaging system 1000, particularly illustrating a storage section 1004 including a probe holder 1006. The portable ultrasound system 1002, storage section 1004, and probe holder 1006 may be substantially similar (e.g., identical) to the portable ultrasound system 502, storage section 520 and/or 530, and any of the probe holders 522-528 and/or 532-538 shown in FIG. 5. Thus, the probe holder 1006 may include an opening 1008 and a slot 1010, where the slot connects extends between the opening 1008 and an exterior surface 1012 of the storage section 1004.

In order to couple the wireless charger and mount assembly 800 with the probe holder 1006, an operator may move the locking clip 830 away from the post 822 (e.g., in the direction of arrow 950 shown in FIG. 9) and position the post 822 of the mount 806 in the opening 1008 of the probe holder 1006. Positioning the post 822 in the opening 1008 may include inserting the post through the slot 1010, in one example. In other examples, positioning the post in the opening 1008 may include positioning the post 822 above the opening and inserting the post into the opening via the top of the opening 1008. Further, the post 822 of the mount is positioned in the opening such that the locking clip 830 is positioned outside of the probe holder 1006 (e.g., outside of the opening 1008 and the slot 1010) proximate the exterior surface 1012 of the storage section 1004.

Upon positioning the post 822 of the mount 806 in the opening 1008 of the probe holder 1006, the operator may release the locking clip 830, such that the biasing member 840 urges the locking clip towards the post 822. Thus, as illustrated in FIG. 10, the locking clip 830 is pressed against the exterior surface 1012 of the storage section adjacent the probe holder 1006, so that the mount 806 is coupled (e.g., clipped on) to a section of the storage section 1004 disposed between the opening 1008 and the exterior surface 1012. In this way, the mount 806 can be automatically locked in a desired position in a probe holder of the portable ultrasound system, allowing an operator to quickly and easily couple and decouple assembly 800 from the probe holder as desired. Thus, the ultrasound probe 802 may be placed on the wireless charger 804 for charging, as demanded, in a convenient location proximal to the portable ultrasound system 1002.

FIGS. 1-10 provide for a method for mounting a wireless charging assembly on an ultrasound imaging system. The method includes exerting a force on a locking member of a mount and inserting a post of the mount in an elongated opening of a probe holder of a portable ultrasound workstation or device (e.g., by manipulation of an operator). Next, the method includes removing the force exerted on the locking member to releasably couple the mount with the probe holder. For instance, the steps of exerting and removing said force may involve an operator manipulating the locking member 228, as shown and discussed with respect to FIGS. 6-7 or the locking clip 830, as described with respect to FIGS. 9-10, in different examples described herein. The method further includes coupling a wireless charger to the mount via an interface formed on a first surface of the wireless charger and positioning a wireless ultrasound probe on a second surface of the wireless charger opposite the first surface.

In this way, the wireless charger and mount assemblies 200 and 800 described herein with regard to FIGS. 2-7 and 8-10, respectively, may provide reliable, easy-to-use locking mechanisms and arrangements for allowing the assembly to be quickly coupled and decoupled from a portable ultrasound system. Further, the mounting systems are designed so as to be usable with a variety of different shapes and sizes of probe holders, thereby providing an adaptable assembly that can be used in a variety of different environments or systems. Further, the wireless charger and mount assemblies may be easily assembled or disassembled (e.g., for cleaning), which may reduce time associated with assembling the components of the wireless charger and mount assembly.

FIGS. 2-10 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The invention will be further described in the following paragraphs. In one aspect, a wireless charging assembly is provided that comprises a wireless charging assembly comprising a mount; a wireless charger having a first surface, the wireless charger releasably coupled to the mount, the mount including a coupling mechanism for releasably coupling the mount to a holder of a medical device; and the wireless charger holder configured to hold and wirelessly charge a rechargeable electronic device placed on the first surface.

In another aspect, an ultrasound imaging system is provided that comprises a portable ultrasound imaging console comprising: a controller in electronic communication with a display; and a housing enclosing the display and the controller, the housing including a storage section having a first opening extending between a first surface of the storage section and a second surface of the storage section opposite the first surface; a wireless ultrasound probe in wireless electronic communication with the controller; and a wireless charging assembly configured to releasably couple with and wirelessly charge a power source of the wireless ultrasound probe and the first opening of the storage section.

In yet another aspect, a method for mounting a wireless charging assembly on a portable ultrasound imaging system is provided, the method comprising exerting a force on a locking member of a mount and inserting a post of the mount in an elongated opening of a probe holder of a portable ultrasound workstation; removing the force exerted on the locking member to releasably couple the mount with the probe holder, subsequent to exerting the force and inserting the post in the elongated opening; coupling a wireless charger to the mount via an interface formed on a first surface of the wireless charger; and positioning a wireless ultrasound probe on a second surface of the wireless charger opposite the first surface. In one example, inserting the post of the mount in the elongated opening of the probe holder may further include inserting the post through an elongated slot of the probe holder that is in communication with the elongated opening. In another example, exerting the force on the locking member may include overcoming a biasing force of a biasing member disposed between the locking member and the post. Further, in one example, the locking member may include a sliding member positioned for axial movement within the post and the biasing member is a compression spring. In yet another example, the locking member may include a locking clip pivotally coupled to the post by a rotation shaft and the biasing member is a torsion spring. In another example, In any of the aspects or combinations of the aspects, the wireless charger may be releasably coupled to the mount via an interface, the interface including a clip positioned on a second surface of the wireless charger, opposite the first surface, configured to engage a mating feature formed on the mount.

In any of the aspects or combinations of the aspects, the coupling mechanism may include a spring disposed between a first portion of the mount and a second portion of the mount that is movable relative to the first portion.

In any of the aspects or combinations of the aspects, the spring may be a compression spring.

In any of the aspects or combinations of the aspects, the spring may be a torsion spring.

In any of the aspects or combinations of the aspects, the mating feature may be formed on the first portion of the mount.

In any of the aspects or combinations of the aspects, the wireless charger may be releasably coupled to the mount via an interface, and the coupling mechanism of the mount may be operable to releasably secure at least a portion of the mount within an elongated opening of the holder.

In any of the aspects or combinations of the aspects, the first surface of the wireless charger may include at least one retaining feature configured for releasably securing the rechargeable electronic device to the wireless charger.

In any of the aspects or combinations of the aspects, the rechargeable electronic device may be a wireless ultrasound probe, and the medical device may be an ultrasound console.

In any of the aspects or combinations of the aspects, the wireless charging assembly may include a mount including a locking mechanism for selectively locking at least a portion of the mount within the first opening; and a wireless charger including a first interface on a first surface of the wireless charger configured to releasably couple with the mount, and a second interface on a second surface of the wireless charger opposite the first surface configured to releasably couple with the wireless ultrasound probe.

In any of the aspects or combinations of the aspects, the mount includes a first portion having a tab protruding therefrom and section configured to engage with the first interface of the wireless charger.

In any of the aspects or combinations of the aspects, the locking mechanism may include a spring biasing a first portion of the mount relative to a second portion of the mount, wherein one of the first portion and the second portion is positioned within the first opening, and the spring biases the other of the first portion and the second portion to releasably couple the wireless charging assembly with the storage section of the housing.

In any of the aspects or combinations of the aspects, the mount may include a slider axially movable within an elongated hollow post and a base coupled to an end of the slider that extends outward from the hollow post, and the locking mechanism may include a spring disposed within the hollow post between the slider and the hollow post, wherein the hollow post and slider positionable within the first opening such that a portion of the storage section is held between the base and the hollow post.

In any of the aspects or combinations of the aspects, the mount may further include a second portion coupled to the first portion and positionable within the first opening, wherein the second portion is coupled to a third portion of the base via the locking mechanism, and the locking mechanism includes a torsion spring configured to bias the third portion towards the second portion to releasably couple the wireless charging assembly with the storage section of the housing.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A wireless charging assembly comprising:
a mount; and
a wireless charger having a main body portion and at least two arms, the wireless charger releasably coupled to the mount, the mount including a coupling mechanism for releasably coupling the mount to a holder of a medical device, the wireless charger configured to hold and wirelessly charge a rechargeable electronic device placed on a first surface of the main body portion, wherein the wireless charger holds the rechargeable electronic device via the at least two arms, wherein the at least two arms extend from opposing sides of the first surface and away from a second surface of the wireless charger, opposite the first surface, wherein each of the at least two arms curves inward toward a midline of the first surface, and wherein the first surface is in direct physical contact with a face of the rechargeable elec- tronic device, wherein the face is adjacent to an end of the rechargeable electronic device that contacts a patient during use.

2. The wireless charging assembly of claim 1, wherein the wireless charger is releasably coupled to the mount via an interface, the interface including a clip positioned on the second surface of the wireless charger, opposite the first surface, configured to engage a mating feature formed on the mount.

3. The wireless charging assembly of claim 2, wherein the coupling mechanism includes a spring disposed between a first portion of the mount and a second portion of the mount that is movable relative to the first portion, and wherein the mating feature is formed on the first portion of the mount.

4. The wireless charging assembly of claim 3, wherein the spring is a compression spring.

5. The wireless charging assembly of claim 1, wherein the wireless charger is releasably coupled to the mount via an interface, and wherein the coupling mechanism of the mount is operable to releasably secure at least a portion of the mount within an elongated opening of the holder.

6. The wireless charging assembly of claim 1, wherein the rechargeable electronic device is a wireless ultrasound probe, and wherein the medical device is an ultrasound consol.

7. The wireless charging assembly of claim 1, wherein the at least two arms are integrally formed with a body of the wireless charger.

8. The wireless charging assembly of claim 1, wherein the at least two arms are formed of a flexible material.

9. The wireless charging assembly of claim 1, wherein the rechargeable electronic device is positioned between and in direct contact with the at least two arms.

10. The wireless charging assembly of claim 9, wherein each of the at least two arms connect to the main body along a segment, wherein a length of the main body is greater than the segment, and wherein the length and the segment each have two ends, and wherein the two ends of the segment are located between the two ends of the length.

11. An ultrasound imaging system comprising:
 a portable ultrasound imaging console comprising:
  a controller in electronic communication with a display; and
  a housing enclosing the display and the controller, the housing including a storage section having a first opening extending between a first surface of the storage section and a second surface of the storage section opposite the first surface;
 a wireless ultrasound probe in wireless electronic communication with the controller; and
 a wireless charging assembly configured to releasably couple with and wirelessly charge a power source of the wireless ultrasound probe and to releasably couple with the first opening of the storage section, wherein the wireless charging assembly includes:
  a mount including a locking mechanism for selectively locking at least a portion of the mount within the first opening; and
  a wireless charger including:
   a first interface on a first surface of the wireless charger configured to releasably couple with the mount, and
   a second interface on a second surface of the wireless charger opposite the first surface configured to releasably couple with the wireless ultrasound probe, wherein power is transmitted to the wireless ultrasound probe through the second surface;
 wherein the mount includes a first portion having a feature configured to engage with the first interface of the wireless charger.

12. The ultrasound imaging system of claim 11, wherein the wireless ultrasound probe and the wireless charger couple at the second interface via at least two arms that extend from opposing sides of the second surface of the wireless charger and away from the first interface, and wherein each of the at least two arms curves inward toward a midline of the second surface.

13. The ultrasound imaging system of claim 11, wherein the feature is a tab protruding from the first portion configured to engage with a clip on the wireless charger.

14. The ultrasound imaging system of claim 11, wherein the locking mechanism includes a spring biasing a first portion of the mount relative to a second portion of the mount, wherein one of the first portion and the second portion is positioned within the first opening, and the spring biases the other of the first portion and the second portion to releasably couple the wireless charging assembly with the storage section of the housing.

15. The ultrasound imaging system of claim 11, wherein the mount includes a slider axially movable within an elongated hollow post and a base coupled to an end of the slider that extends outward from the hollow post, and the locking mechanism includes a compression spring disposed within the hollow post between the slider and the hollow post, wherein the hollow post and slider positionable within the first opening such that a portion of the storage section is held between the base and the hollow post.

16. A method for mounting a wireless charging assembly on a portable ultrasound imaging system, the method comprising:
 exerting a force on a locking member of a mount and inserting a post of the mount in an elongated opening of a probe holder of a portable ultrasound workstation;
 removing the force exerted on the locking member to releasably couple the mount with the probe holder, subsequent to exerting the force and inserting the post in the elongated opening;
 coupling a wireless charger to the mount via an interface formed on a first surface of the wireless charger; and
 positioning a wireless ultrasound probe on a second surface of the wireless charger opposite the first surface.

17. The method of claim 16, wherein exerting the force on the locking member includes overcoming a biasing force of a biasing member disposed between the locking member and the post.

18. The method of claim 17, wherein the locking member includes a sliding member positioned for axial movement within the post and the biasing member is a compression spring.

19. The method of claim 16, wherein inserting the post of the mount in the elongated opening of the probe holder further includes inserting the post through an elongated slot of the probe holder that is in communication with the elongated opening.

* * * * *